(12) United States Patent
Stafford et al.

(10) Patent No.: US 6,224,831 B1
(45) Date of Patent: May 1, 2001

(54) MICROASSAY DEVICE AND METHODS

(75) Inventors: Alan P. Stafford, North Ridgeville, OH (US); H. Kevin Smith, Latrobe, PA (US); David Yarnes, Jamestown, NY (US)

(73) Assignee: John Co., Inc., Gowanda, NY (US)

( * ) Notice: Subject to any disclaimer, the term of this patent is extended or adjusted under 35 U.S.C. 154(b) by 0 days.

(21) Appl. No.: 09/052,237

(22) Filed: Mar. 31, 1998

(51) Int. Cl.[7] .......................... G01N 33/94; G01N 33/53; G01N 33/535

(52) U.S. Cl. ............................ 422/101; 422/56; 435/4; 435/287.8; 435/288.7; 436/530; 436/528; 436/535; 436/169; 436/170; 436/901; 436/805

(58) Field of Search ................................ 422/56, 58, 101; 435/4, 287.1, 287.8, 288.7; 436/169, 170, 172, 805, 518, 528, 529, 531, 535, 901

(56) References Cited

U.S. PATENT DOCUMENTS

| | | |
|---|---|---|
| 4,459,358 | 7/1984 | Berke . |
| 5,196,302 | 3/1993 | Kidwell . |
| 5,200,321 | 4/1993 | Kidwell . |
| 5,369,007 | 11/1994 | Kidwell . |
| 5,686,315 | * 11/1997 | Pronovost et al. . |
| 5,772,961 | * 6/1998 | Mico . |

FOREIGN PATENT DOCUMENTS

| | | |
|---|---|---|
| 0066648 | 12/1982 | (EP) . |
| 0279097 | 8/1988 | (EP) . |
| 0283613 | 9/1988 | (EP) . |
| 0605828 | 7/1994 | (EP) . |

* cited by examiner

*Primary Examiner*—Deborah Jones
*Assistant Examiner*—Jennifer McNeil
(74) *Attorney, Agent, or Firm*—Saliwanchik, Lloyd & Saliwanchik

(57) ABSTRACT

The subject invention relates to a rapid, field-portable, modular, versatile and highly reliable assay device for substances, particularly drugs of abuse, which provides a positive signal in the presence of a specific substance for which the device has been specifically adapted to test. The subject invention also concerns methods for making and using the assay device. The device is easily and reliably manufactured by laminating a series of manufactured layers to each other to form an upper card assembly and a lower card assembly. The upper card assembly is bonded to the upper side of a layer which has an immobilized reagent specific for a test substance bound thereto, and the lower card assembly is bonded to the lower side of the layer having the immobilized reagent. The device can be manufactured and distributed in a unitary, ready-to-use form. Additionally, the upper and lower card assemblies can be bonded to any specific reagent layer of choice in the field, depending on the needs of any particular test to be conducted.

18 Claims, 3 Drawing Sheets

MICROASSAY DEVICE AND METHODS

FIELD OF THE INVENTION

This invention relates to a rapid, field-portable, modular, versatile and highly reliable assay device for substances, particularly drugs of abuse, and a method for making and using the device which provides a positive signal in the presence of a specific substance for which the device has been specifically adapted to test.

BACKGROUND OF THE INVENTION

U.S. Pat. Nos. 5,369,007, (hereinafter the '007 patent) and 5,200,321 (hereinafter the '321 patent), disclose a microassay on a card. In addition, a review of other devices and methods of microassay was provided in the '007 and '321 patents. The disclosure of those patents and the art cited therein is hereby incorporated by reference.

The '007 patent discloses a microassay card for detecting the presence of particular test substance in a liquid sample. The microassay card disclosed in the '007 patent consists of at least the following four functional layers of materials:

A. A paper label which can be eliminated if layer B has a printable or writable surface;

B. A well contained within a hydrophobic layer for receipt of a liquid test sample;

C. A supporting layer which is a substrate for a reagent that comprises either an anti-substance-enzyme conjugate bound to a substance which is immobilized on said layer or a substance-enzyme conjugate bound to an anti-substance which is immobilized on said layer;

D. A semi-permeable layer which controls the rate at which the test solution is able to leave the upper layers and enter the bottom layer;

E. A super-absorbent layer, which draws sample liquid down through the various layers of the device, containing a chromogenic substrate which changes color upon contact with either enzyme-conjugated antibody or enzyme-conjugated test substance released from the upper layers, depending on the nature of the moiety immobilized in layer C.

The instant disclosure provides a device and method similar in some respects to the device and method disclosed and claimed in the '007 patent. However, several novel features and improvements are provided herein such that the device of the instant invention is modular, in the sense that unitary portions of the device are separately manufactured and can be pre-assembled by the manufacturer for analysis of a particular analyte, or may be assembled in the field by the user, and thereby adapted for analysis of a wide range of analytes. In addition, because of novel features in the manufacture of the device of this invention, the reliability of the instant device is enhanced.

The '007 patent contains little disclosure about how the card can be manufactured and assembled. The disclosure concentrates on what is contained within each of the several layers. There is no teaching or suggestion of ways in which a particular device, once manufactured, could be modified to test for different substances based on the needs of the user. There is also no teaching or suggestion of a modular device which can be either pre-assembled or assembled in the field using highly reliable upper and lower card assemblies. Accordingly, from the disclosure of the '007 patent, one of ordinary skill in the art would understand that a different card would need to be specifically manufactured or purchased for each substance to be tested or each set of substances to be tested, or the card as purchased would need to have several wells, each pre-prepared for analysis of a particular test substance.

BRIEF SUMMARY OF THE INVENTION

The present invention concerns a modular microassay device comprising an upper card assembly and a lower card assembly which can be combined to form a microassay card. In one embodiment, the upper card assembly, which can be used for any microassay card so long as instructions imprinted thereon are modified or are modifiable, includes several layers with concentric holes in each layer such that a test sample can be placed in the wells formed by the alignment of the concentric holes in the several layers of the upper card assembly. In a preferred embodiment of the upper card assembly, these layers include:

Layer 1: An imprintable label; this layer may be absent if layer 2 is printable; only the printing needs to be changed for the upper card assembly to be used in the production of a microassay card having any desired specificity, as defined by layer 4 (see below).

Layer 2: A plastic sheet.

Layer 3: A high tack, pressure-sensitive adhesive layer having a removable covering.

In one embodiment, the lower card assembly, which can be used for assembly of any microassay card, consists of several layers with concentric holes that can be aligned with those holes in the upper card assembly. In a preferred embodiment of the lower card assembly, these layers include:

Layer 5: A plastic sheet.

Layer 6: A semi-permeable membrane.

Layer 7: A super-absorbent layer preferably containing a chromogenic enzyme substrate.

Layer 8: A plastic sheet.

Prior to final assembly of the upper and lower card assemblies to form a complete microassay card, the user or manufacturer selects a layer of test substance-specific material, for interposition between the upper card and lower card assemblies. This interposed layer, referred to herein as Layer 4, is preferably a cellulose-based material onto which is immobilized a reagent, such as an antibody which has bound to it its corresponding enzyme conjugated test substance, or a test substance which has bound to it its corresponding enzyme conjugated antibody. It is this feature which provides the user the option of adapting the card to test any substance for which a test substance-specific layer is available.

The subject invention also provides a method of mass producing the card components and mass assembly of cards adapted to different biochemical analyses, by using the same upper and lower card assemblies and changing only layer 4 for detection of a specific test substance.

Accordingly, it is an object of the invention to provide a rapid, field-portable, modular, versatile and highly reliable assay device adapted to test for specific substances, such as drugs of abuse and chemicals. In use, the subject device provides a positive signal in the presence of a specific substance. It is understood that the subject device, by selecting the appropriate antibody or antigen, can be utilized for other analysis tests, such as, for example, for the detection of water impurities, agricultural related tests for bacteria, traces of medication, pregnancy test, and tests used in pathology and medical fields.

Another object of the invention is to provide a method for making a rapid, field-portable, modular, versatile and highly reliable assay device for detecting substances, such as drugs and chemicals, wherein the device provides a positive signal in the presence of a specific substance for which the device has been specifically adapted to test.

Another object of the invention is to provide a method for using a rapid, field-portable, modular, versatile and highly reliable assay device to test for specific substances, such as drugs and chemicals, wherein the method provides a positive signal in the presence of a specific substance for which the device has been specifically adapted to test.

DETAILED DESCRIPTION OF THE DRAWINGS

DETAILED DESCRIPTION OF THE INVENTION

The subject invention concerns a modular assay device adapted for detecting specific substances, such as drugs and chemicals, in a test sample. The device and methods of the present invention are particularly useful for the detection of drugs of abuse such as, for example, cocaine, LSD, PCP, heroin, morphine and the like. In one embodiment, the assay device comprises an upper card assembly and a lower card assembly which can be combined with a test substance-specific layer of material interposed between the upper and lower assemblies to form a fully functional assay device.

Figure 1:
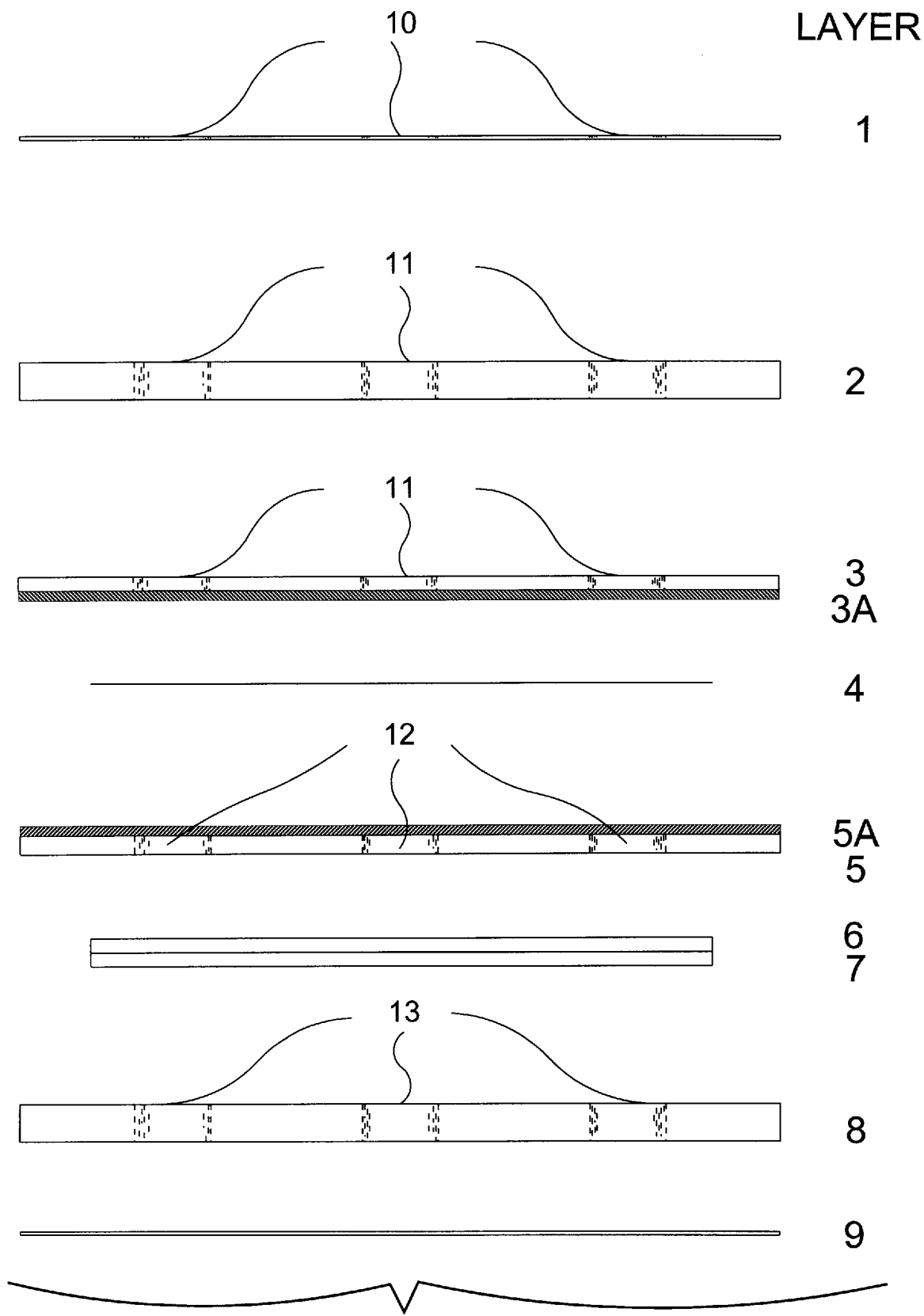
FIG. 1 illustrates, in an exploded view, the different components of a laminated card of the subject invention.

With reference to FIG. 1, an exploded view of one embodiment of the assay device or card of this invention is disclosed. A first layer 1 of the card is a paper label on which instructions can be printed and where the user can make annotations to identify tested specimens. Layer 1 is optional, so long as the second layer, layer 2, is composed of a material that is printable or has a writable surface. Thus, where an assay device of the present invention has a layer 2 which can be printed or written on, then layer 1 is optional, and can be present or absent, depending on the preference of the user or manufacturer.

Layer 2 can be a plastic or other liquid impermeable sheet, preferably having a thickness between about 0.02 inches and 0.25 inches. The next layer, layer 3, comprises a high-tack, pressure sensitive adhesive layer. Optionally, layer 3 can have a removable covering, 3A, which can be peeled from layer 3 to reveal the adhesive surface.

The second and third layers, 2 and 3 respectively, have concentric holes 11 of essentially equal diameter. Layer 1 has holes 10, concentric with holes 11 in the second and third layers, but the holes 10 may have a slightly larger diameter than the holes 11, or may have the same diameter. Preferably, the diameter of the holes 11 is from about 0.2 inches to about 0.4 inches, to accommodate easy application of fluid samples to the sample wells created by the concentric holes in the several layers of the device when the layers are affixed to each other and the holes are in alignment with each other. The number of holes formed in the device is not critical and depends on the particular assay for which the device is being used. Typically, a device of the present invention may have three holes, as exemplified in FIG. 1, thereby providing a test well for the sample to be tested, a negative control well and a positive control well in the assay device.

In a first embodiment of this invention, referred to herein as embodiment A, the combination of layers 1, 2, and 3 having holes 10 and 11 to form wells, is referred to herein as the "upper card assembly," and is a modular unit. In a second embodiment of this invention, referred to herein as embodiment B, in addition to layers 1, 2, and 3, the upper card assembly also comprises a layer 4, as described herein. Layer 4 is attached to the underside of layer 3.

Layer 4 contains a reagent that can specifically interact with a particular test substance. The reagent contained in layer 4 is immobilized on or within a liquid permeable support, such as a membrane which forms the layer. Preferably, the membrane is composed of cellulose, nitrocellulose, or like substances. Layer 4 spans the wells formed by holes 10 and 11 in layers 1, 2 and 3. The specific reagent in layer 4 preferably completely coats the surface area of layer 4 that lies within the well created by holes 10 and 11 in layers 1, 2 and 3. In order to preserve valuable specific binding reagent, the remainder of layer 4 that is not located within the well but which is sandwiched between the upper layers and the lower layers, as described herein, need not be coated with or contain the specific binding reagent.

Preferably, layer 4 contains antibodies which specifically bind a particular biochemical substance, such as an illicit drug or any other hapten or molecule for which specific antibodies are available. The antibodies may be monoclonal antibodies, polyclonal antibodies and may be portions of antibodies which specifically interact with antigens, such as Fab or Fv fragments. Antibodies may be from any species. Those skilled in the art will recognize, however, that any molecule which is capable of specifically interacting with another molecule can be used in this layer. For example, nucleic acids which are capable of hybridizing with nucleic acids in a test sample could be located in this layer. Other examples of reagents useful in the assay device include nucleic acid binding proteins, lectins, biotin, avidin, and protein A, each of which have art-recognized ligands with which they specifically interact.

The portion of layer 4 which is within the wells formed by holes 10 and 11 is preferably in intimate contact with that portion of layer 6 which is also within the well and directly beneath layer 4. This intimate contact is possible because layer 5 is relatively thin as is explained in more detail below. This aspect enhances the reliability of the device of the instant invention, and the manner of achieving this enhanced intimate contact is further described herein. As a result of this improvement, the reliability of fluid transfer from the well above layer 4 through the layer is enhanced.

The next layer, 5, includes a liquid impermeable layer made of, for example, plastic, polyester, polyethylene, polystyrene or like substance. This layer is preferably on the order of about 0.001 inches to about 0.1 inches in thickness and has holes 12 therein having a diameter ranging from about 0.1 to about 0.7 inches which are concentric with holes 10 and 11 in layers 1, 2, and 3 of the upper card assembly. Optionally, layer 5 can have a high-tack, pressure sensitive adhesive which can be covered by removable covering 5A. Removable cover 5A can be peeled from layer 5 to reveal the adhesive surface.

In intimate contact with the underside of layer 5, there is a further layer 6 which comprises a semipermeable membrane. Layer 6, and layer 7 which is described in more detail below, span the wells formed by holes 12 in layer 5. Preferably, the membrane material used for layer 6 provides consistent pore sizes and pore densities, thereby yielding microassay devices with similar reaction times. In a preferred embodiment, layer 6 comprises a polycarbonate membrane. This layer retards the rate of fluid transfer through layer 4, in order to provide analyte in the test sample and specific reagent immobilized on layer 4 sufficient contact time for the desired reaction to occur. Layer 6 is required to be in intimate contact with layer 5, and layer 5 in turn is in intimate contact with layer 4. This close association provided for between layers 4 and 6 ensures that the test fluid will remain in the presence of the immobilized reagents in layer 4, and not trapped in a bubble area between layer 4 and layer 6. The intimate contact between these layers therefore ensures that the solution being tested remains in contact with layer 4 long enough for the desired reaction to occur with the immobilized reagent, and thus avoiding problems associated with having the solution passing through quickly to reside in a defect gap or pocket between layers 4 and 6.

Below layer 6, and in intimate contact therewith, a further layer 7 is provided which comprises a superabsorbent material. In a preferred embodiment, the superabsorbent material contains a chromogenic enzyme substrate. In one embodiment, the superabsorbent material is sandwiched between two polymeric layers, such as, for-example, cellulose or polyester. Preferred superabsorbent materials for this purpose include, for example, polymeric compounds capable of binding a large mass of water per unit mass of polymer. Specific examples of such superabsorbent polymers include, but are not limited to, polyacrylic acid and grafted acrylic acid on a carbohydrate backbone. Other superabsorbent materials are known in the art. Examples of superabsorbent materials are described in U.S. Pat. No. 5,369,007, the disclosure of which is herein incorporated by reference. Once hydrated, the superabsorbent polymer should be essentially transparent. The chromogenic enzyme substrate is selected so as to be capable of reaction with an enzyme-linked reagent used with the device and methods of the present invention.

Layer 6, the semipermeable membrane, is required to be in intimate contact with layer 7, so that the fluid transfer from layer 6 to layer 7 is not retarded by the formation of air pockets or other layer interface imperfections. To accomplish this intimate contact, layers 6 and 7 are laminated together during a separate operation. Any technique which does not adversely affect either the semipermeable membrane nature of layer 6 or the superabsorbent nature of layer 7 can be used. An example of a laminating technique useful for lamination of layers 6 and 7 is the application of a thin film of an adhesive to the surfaces of layer 6 and/or layer 7, followed by the application of pressure. Another laminating technique that can be used is the partial melting or softening of layer 6 and/or 7 by heating in conjunction with the application of pressure. The lamination of layers 6 and 7 is particularly advantageous for enhancing reproducibility of results and providing a device which yields consistent microassay device test times.

Provided for beneath layer 7 is a further layer, layer 8, made of plastic, polyester, polyethylene or like material having a thickness of about 0.001 inches to about 0.1 inches with holes 13 having a diameter ranging from about 0.1 inches to about 0.7 inches which are concentric with the holes 12 in layer 5. Layer 8 can be composed of any suitable material, such as, for example, clear plastic, and can have reverse printing directions or patterns thereon to identify wells as, for example, test sample well, positive control well and negative control well. This layer may also be used to obstruct the visibility of portions of layer 7. Optionally, a clear layer 9, attached to layer 8, can be used to protect exposed layer 7 in holes 13.

In a third embodiment of the subject invention, referred to herein as embodiment C, layers 5, 6, 7, and 8 are intimately attached, sealed or laminated together to form a modular unit comprising these layers, referred to herein as the "lower card assembly." In this embodiment, layer S has a high-tack, pressure sensitive adhesive surface, having a removable covering, 5A, which can be peeled from layer 5 to reveal the adhesive surface. This can eliminate the need for an adhesive on layer 3 of an upper card assembly of the invention.

In a fourth embodiment of this invention, referred to herein as embodiment D, in addition to layers 58, the lower card assembly also comprises the layer 4, which is bonded to layer 5 during the manufacturing process.

Holes 10, 11, 12 and 13 described above are typically circular in nature. Some or all of the holes may instead have a different shape such as square, rectangle, triangle, and the like. Different shaped holes used on the same card can help the user to distinguish between control holes and test holes.

In practice, those skilled in the art will recognize that the present invention provides a great deal of flexibility in both the manner of making and using the various embodiments of the assay device of this invention. Thus, for example, the entire operative device comprising an upper card assembly and a lower card assembly with layer 4 in a sealed unit may be assembled by combining the various embodiments of the upper and lower card assemblies. Accordingly, upper card assembly, embodiment A, and the lower card assembly, embodiment C, neither of which comprises layer 4, can be mass produced. In the field, any upper card assembly of embodiment A may be combined with any lower card assembly of embodiment C, and any layer 4 having a reagent with the desired specificity for any given test substance can be interposed between the upper and lower card assemblies. Layer 4 material can be sandwiched between the upper card assembly and the lower card assembly prior to conducting a substance identification test in the field. This is accomplished by adhering layer 4 to either an upper or lower card assembly after removing the protective removable covering 3A or 5A. The adhesive surface of the other half of the device is then affixed to layer 4 to form the complete, operative device. This assembly process can also be conducted to produce the complete device prior to shipment for use in the field, wherein each unit will have a pre-determined specificity ready for use with no field-assembly required.

The complete device can be assembled from other combinations of the upper and lower assemblies. For example, an upper card assembly, as disclosed in embodiment B, which already comprises layer 4, can be assembled with a lower card assembly, embodiment C. Alternatively, an upper card assembly, as disclosed in embodiment A, can be assembled with a lower card assembly, embodiment D, which already comprises layer 4.

Once assembled, a given test sample is either used directly if it is a fluid sample, or is hydrated or contacted with a suitable solution, such as water, prior to testing if it is a non-fluid sample. For example, if a sample of a powder must be tested for cocaine content, a small quantity of the powder is hydrated and then tested. A known positive control containing cocaine could be added to the positive control well, and the solution used to hydrate the unknown sample could be added to the negative control well. Alteratively, for a positive control well a small amount of the substance being tested for or a substance derivative can be impregnated in layer 4 of the positive control well. By initial gravitational and capillary action, the fluid samples wet layer 4 and begin to migrate through the semi-permeable layer 6. Upon reaching layer 7, the fluid is drawn through layers 4 and 6 as the superabsorbent material of layer 7 begins to hydrate.

Once all the fluid added to the test wells has been absorbed, the assay device can be inverted for reading of the result. The presence of a positive test substance will result in the change of color in a dye present in the superabsorbent layer near the bottom of the test well of the device. As a check that a card is working properly, the bottom of the positive control well should change color and the bottom of the negative control well should not change color. If, during the use of an assay device of the present invention, the results for one or both of the control wells do not conform to control standards, then the test results are not reliable.

In preparing layer 4 of this device, as disclosed above, any molecule capable of specifically interacting with the test substance for which the analysis is being conducted can be utilized. The mode of detection can be through a displacement reaction of specific test substance pre-bound to the reagent of layer 4. For example, a cocaine specific antibody may be bound to layer 4, and enzyme-linked cocaine molecules pre-bound to the antibody. Upon addition of a fluid containing cocaine to a test well in the subject device, the pre-bound, enzyme-linked cocaine is displaced and then drawn through layers 4 and 6 and into the superabsorbent layer 7 where the enzyme reacts with a chromogenic dye included in the superabsorbent layer. Alternatively, the mode of detection can be through a competition reaction. In this event, again using cocaine as the example, a layer 4 containing immobilized cocaine molecules is used in the assay device. Enzyme-linked, cocaine specific antibody is then added to the test solution which is then added to the test well and thereby drawn through layer 4. If the test solution does not contain cocaine, all or substantially all of the enzyme linked antibody will bind to the immobilized cocaine in layer 4 and the test well will read as negative because little or no enzyme-linked antibody is drawn into the superabsorbent layer containing chromogenic reagent. On the other hand, if cocaine is present in the test solution, then the cocaine in the sample competes with the immobilized cocaine for binding of the enzyme-linked, cocaine-specific antibody. The more cocaine in the sample, the more enzyme-linked antibody that binds to the free cocaine compared to that bound by the immobilized cocaine. Any enzyme-linked antibody bound to cocaine in the sample is drawn through layers 4 and 6 and into the superabsorbent layer 7 containing the chromogenic enzyme substrate.

Suitable pore sizes for the polycarbonate, polysulfone or like materials for use as membranes of this invention are disclosed in U.S. Pat. No. 5,369,007, and are herein incorporated by reference. Ideal transit times for fluid added to the microassay device are controlled by the pore sizes and pore densities. Ideally, an assay using a device of the present invention can be completed in a relatively short amount of time, preferably between about 20 seconds and 10 minutes, depending on the optimal times required for the various reactants to remain in contact with each other. These parameters can be easily optimized by a skilled artisan for any given test substance and specific immobilized reagent, through routine experimentation utilizing the specifics of the device manufacture process described herein.

The nature of suitable superabsorbent material used in layer 7 may likewise be learned from U.S. Pat. Nos. 5,369,007; 5,200,321; and 5,196,302, the disclosure of which is herein incorporated by reference.

Suitable chromogenic dyes and enzymes for use in this device include any reagents which give a strongly visible reactant product upon contact of the enzyme and the chromogenic dye. Any necessary co-factors for the reaction, such as, for example, a source of hydrogen peroxide, can be included in the superabsorbent layer in the form of sodium peroxide or sodium perborate. Alternatively, hydrogen peroxide could be provided in the aqueous solution used to dissolve or hydrate an unknown substance being tested. Various dyes suitable for use in the subject device are disclosed in U.S. Pat. No. 5,369,007, herein incorporated by reference.

The device of the present invention can be prepared by manufacturing a plurality of layers, each of which performs a specific function, and each of which is laminated to adjacent layers, to result in a multilayered device with each layer being in intimate contact with its adjacent layers. In one embodiment, the method comprises the steps of manufacturing a first, imprintable layer, with a series of holes cut therein. This layer may be made of paper, plastic or any other suitable material which will accept appropriate markings to identify which sample is placed in each of the holes.

A second layer is manufactured from a liquid impervious material such as plastic, polyethylene, or like material. The layer is prepared with holes such that upon bonding of this layer to the underside of the first layer, the holes in each of the layers come into alignment with each other. The holes in this and the other layers can have any geometric shape and can be formed by any method. However, for ease of manufacture, circular holes which are punched out of the material forming the layer are satisfactory. In an alternative embodiment, several layers are laminated together and holes are punched therein. The number of holes in each layer is not critical, so long as the same number of holes is used in each layer. A device capable of accepting, for example, one to fifty samples, can be readily prepared, with the dimensions of the device having to be scaled accordingly. However, the general method of manufacture and use described herein will be applicable to production of a device with any number of holes. It will also be recognized that, for ease of alignment of the holes in the layers containing holes, it is helpful for each layer to be formed from material having essentially the same dimensions. Thus, a microassay device of the present invention can have any desired dimensions. A device having square dimensions of about 1.5 inches on a side is preferred.

A third layer having a high tack, pressure sensitive lower surface is manufactured for adhesion to the underside of the second layer. The adhesive lower surface of the third layer is preferably protected, for example, by a peelable covering. The third layer is made with holes provided therein such that upon bonding of this third layer to the underside of the second layer, the holes in the third layer register with the holes in the first and second layers. The registered holes of each of these layers form a series of wells of equal number with the number of holes cut in each of the first, second and third layers. An alternative and preferred method would be to initially laminate sheets of these top three layers to form an upper laminated assembly, simultaneously mass punch holes in all three layers of this laminated upper assembly and cut or shear individual cards from the laminated sheet. In use, a fluid sample may be added to each of the wells, the walls of which are formed by the bonded widths of each of the first, second and third layers.

Figure 2A:
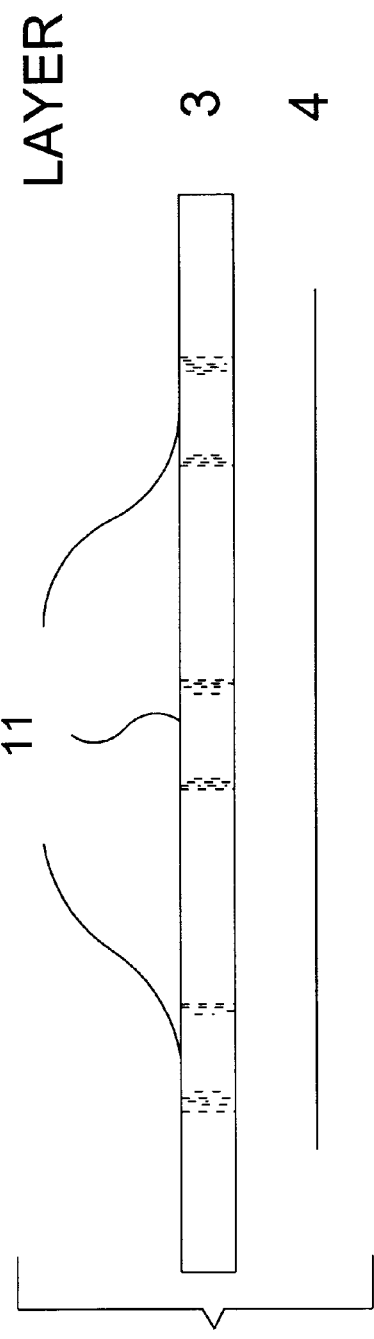
FIG. 2 illustrates an alternate embodiment of layer 4 in which reagent tabs or segments having a selected reagent immobilized to the tab or segment are adhered to a well of the test device.
Figure 2B:
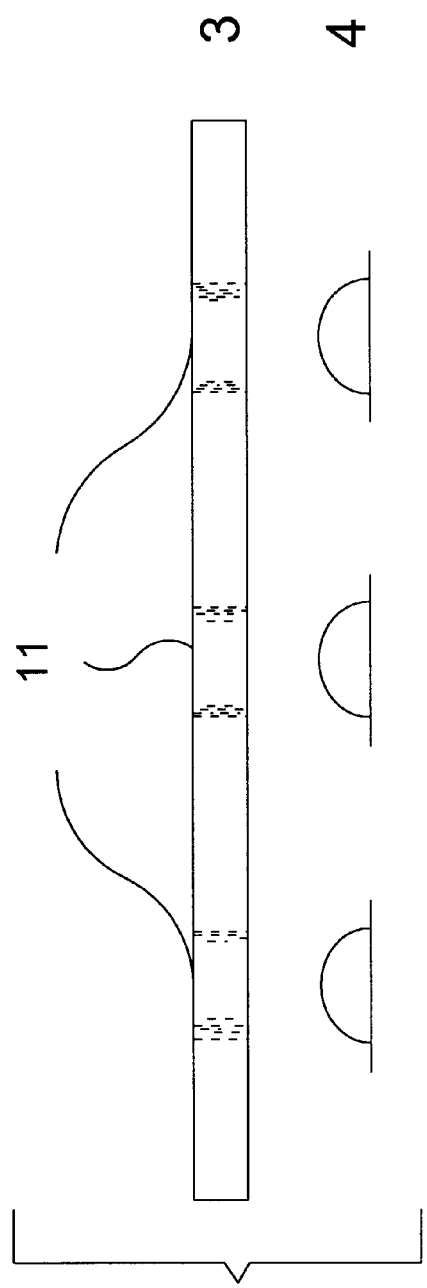
Figure 3:
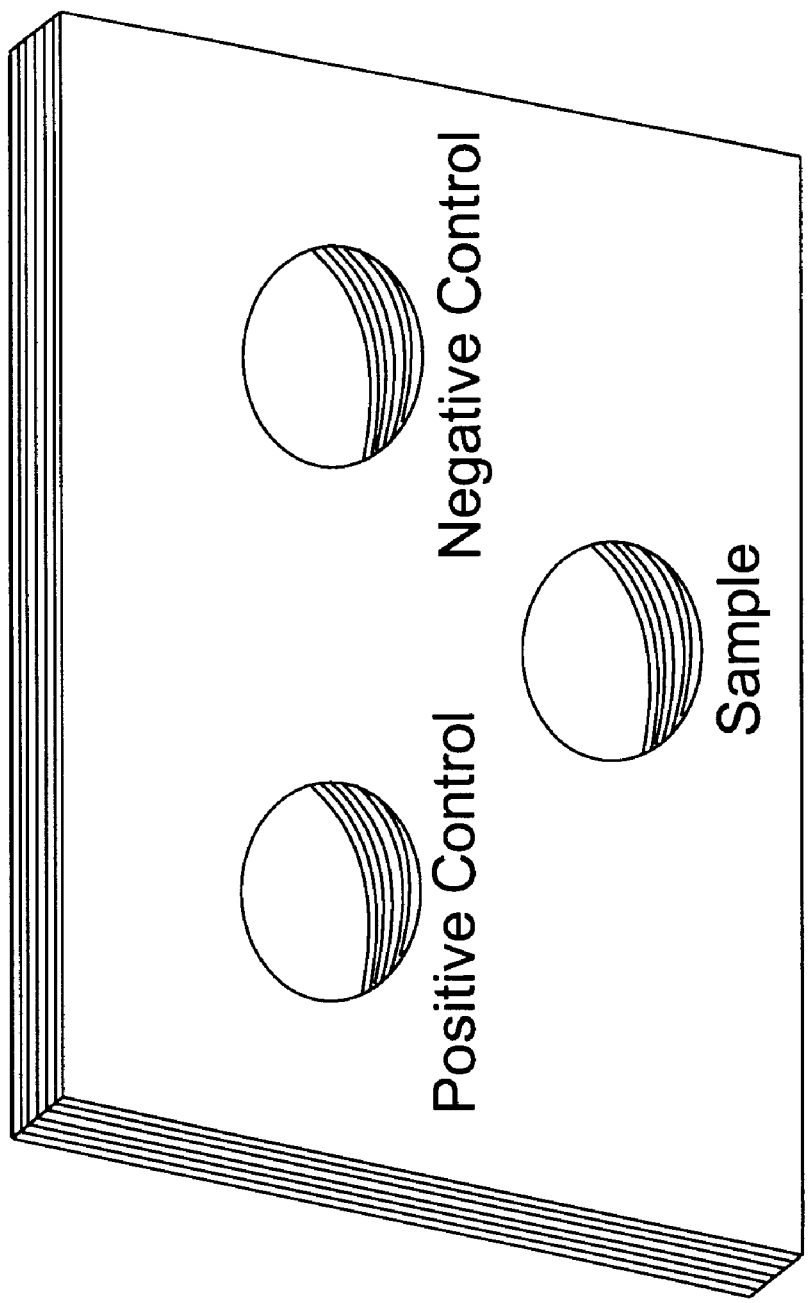
FIG. 3 shows the underside of one embodiment of the assembled device.

A fourth layer, without any holes, is provided which has an immobilized reagent capable of specific interaction with a specific test substance in an added sample. Preferably, the reagent must at least cover an area on the fourth layer which is within the well formed by the holes of the foregoing layers, when the fourth layer is bonded to the underside of the third layer. This is easily accomplished by removing the protective layer from the underside of the third layer and pressing the fourth layer onto the high-tack lower surface of the third layer to form an intimate contact. As a result, any test fluid placed in the wells is forced to come into contact with the reagent on the fourth layer upon passage of the fluid through the fourth layer. As shown in FIGS. 1 and 2, layer 4 can be a unitary membrane with selected reagents immobilized only to the area within and/or near a well (FIG. 1), a unitary membrane with a selected reagent immobilized over the complete membrane (FIG. 1), or segments of membrane with a selected reagent bound thereto (FIG. 2). The segments of membrane can be applied to the underside of each well (FIG. 2). It is necessary for the fourth layer to be sufficiently porous to allow passage of fluid therethrough at a controlled rate. Preferred substances for this layer include, but are not limited to, cellulose, nitrocellulose, and like materials. The membrane can be treated to prevent unwanted movement of solution and/or between wells according to standard methods known in the art.

A fifth layer, for adhesion to the underside of the fourth layer, is manufactured from a liquid impermeable material. The purpose of this layer is to prevent spread of fluid from the fourth layer material into areas of the device where fluid is not desired. Holes are cut in this layer such that the holes register with the holes in the first, second and third layers and the reagent covered area of the fourth layer. In this way, upon permeation of fluid from the wells created by the holes in the first, second and third layers and through the fourth layer, the fluid is directed into the holes of the fifth layer. The fifth layer which can have an upper, high-tack, pressure-sensitive surface which is protected by a peelable protective layer, replacing or complimenting the adhesive described above for the third layer. In this way, the tacky surface of the fifth layer may be exposed by peeling off the protective layer, and the fifth layer can then be bonded to the underside of the fourth layer and/or the third layer.

A sixth layer is manufactured, without any holes, for adhesion to the underside of the fifth layer. The sixth layer is preferably made from a semi-permeable membrane having a pore size and pore density chosen such that the rate of fluid transfer through the fourth layer is metered by the rate at which fluid is able to permeate through the sixth layer. Membranes capable of achieving such metering are known in the art.

A seventh layer is manufactured without any holes, for adhesion to the underside of the sixth layer. The seventh layer is made from a superabsorbent composite layer capable of absorbing a large volume of fluid per mass unit of superabsorbent material. The seventh layer also contains an indicator, such as a chromogenic dye, such that upon absorption of fluid by the superabsorbent material, contact of test substance in the fluid, or contact of a reagent which is present in the fluid in an amount that is proportional to the amount of a test substance in said sample, initiates a color-generating reaction which indicates the presence of test substance in the sample.

A flexible, fluid impermeable eighth layer is manufactured for adhesion to the underside of the seventh layer. The eighth layer is made with the same number of holes as in the preceding layers so that as the superabsorbent material expands upon absorption of fluid, the eighth layer does not impede this swelling. The eighth layer may also form an imprintable backing for the microassay device such that appropriate markings may be made on the backing to indicate which well contains a positive control, a negative control, a test sample or any other appropriate markings.

Each of these layers is bonded to its adjacent layer(s) such that each layer is in intimate contact with its adjacent layer(s). This is critical so that efficient fluid transfer from a well into the superabsorbent layer occurs.

As with the upper assembly, which comprises layers 1, 2, and 3, the lower assembly comprising layers 5, 6, 7, and 8 can be assembled using heat and pressure, or by applying a liquid adhesive and pressure. Preferably, the bottom assembly is laminated in two steps. Layers 6 and 7 are laminated first. Laminated layers 6 and 7 are then laminated between layers 5 and 8. It is preferable that the length and width dimensions of the laminated layers 6 and 7 of the lower assembly be less than the length and width dimensions of layers 5 and 8. Thus, allowing areas of layers 5 and 8 to contact and adhere to each other.

Those skilled in the art will recognize that in this method, a variety of different materials could be used for each of the layers without departing from the operative principle of this invention. It will also be recognized that various of these layers may not be required to obtain a device which operates reliably and efficiently. Thus, for example, the first layer may not be required, particularly when the second layer may be marked with appropriate indications of what samples have been added to which wells. Likewise, layer six may be eliminated if the reaction of test sample and the specific reagent on layer four occurs rapidly, or if layer four sufficiently meters the rate at which fluid permeates into the superabsorbent layer such that further metering by a semi-permeable layer six is not required. The principal requirement of this invention, therefore, is that the device is easily and reproducibly manufactured from layers, each of which performs a specific function, and each of which is or can be intimately bonded to its adjacent layer(s). Furthermore, the ability to independently construct an upper card assembly and a lower card assembly, and to choose any layer four having any desired specificity, gives the method and device of this invention an unprecedented level of flexibility.

It will also be recognized that in preparation of layer four, the quantity of reagent used can be conserved by immobilizing the reagent only to the area of the layer which registers with the wells formed by the upper card assembly. However, it will also be understood that the entire layer can have reagent immobilized thereto for ease of manufacture if quantity or cost of reagent is not a limiting factor.

In selecting the reagent to be affixed to layer four, several considerations should be borne in mind. First, in a modular system where the reagent of layer four can be independently selected from the upper card and lower card assemblies, it is critical to use an indicator system which will operate with any chosen layer four. Accordingly, if layer four is an immobilized antibody which is pre-bound to a particular enzyme-linked test substance, then the super-absorbent layer must contain a chromogenic substrate for the enzyme which will be released if a sample containing the test substance competes with the pre-bound, enzyme-linked substance from the immobilized antibody layer. Whatever co-factors are needed for the enzyme-substrate reaction to occur efficiently must be provided in the superabsorbent layer. Bearing these requirements in mind, it will be clear to those skilled in the art that if a layer having a different pre-bound, enzyme linked substance is used, the requirements of the linked enzyme must be considered If the same linked enzyme is used, the same lower card assembly may be employed as all of the necessary substrates and cofactors will already have been provided for. However, if a different enzyme or indicator system is used, then a different lower card assembly may be required.

Second, with respect to testing of multiple different test samples, and the provision of a positive and negative control, it will be recognized that slightly different components will be required. For multiple identical samples all to be tested for the same suspected test substance, either multiple different devices may be used or a single device with many wells, all of which have the same test-substance specificity, may be used. For the negative control, all that is required is that one of the wells be appropriately marked as such and a critical component of the test eliminated from that well. Thus, for example, in the negative control well, the enzyme substrate may be eliminated from the superabsorbent layer associated with that well. Likewise, the pre-bound test substance may have no enzyme linked thereto, or there may simply be no bound antibody in that well. In this way, should a positive result develop in the negative control well, a fault in the assay will be revealed. In the positive control well, all that would be required would be for a known sample of the suspected test sample to be added to any well on the test device, or preferably, impregnating layer 4 of the positive control well with the known test sample and that well marked "positive control." Should a positive result not be achieved in that well, it would be known that the test is in some way defective.

Given the foregoing description of the manner in which the microassay device of the instant invention is produced, those skilled in the art will recognize that a novel device is thereby produced which has several desirable features. These include, but are not limited to: the ability to cost-effectively produce the device on a commercial scale; the ability to produce a modular device which may be assembled in the field and which may be adapted to test for any particular test substance for which a specific layer four having suitable selected immobilized reagent is available; and the ability to produce an assay device having improved reliability due to the intimate contact between various layers.

Bearing in mind the novel features of this method and device, those skilled in the art will further recognize that, in comparison to the test device of U.S. Pat. No. 5,369,007, for example, certain improvements have been made. Namely, in a microassay device for assaying a suspected substance in a liquid sample comprising:

a. a first section, referred to herein as the upper assembly, identified above as layer 2 or second layer, comprising a hydrophobic, liquid impermeable portion having formed therein at least one well for receiving a liquid sample;

b. a second section, identified above as layer 4 or fourth layer, defining a bottom surface of the formed well, comprising a supporting surface of cellulose which directly and covalently binds and supports thereon a reactive reagent, wherein this second section is in contact with a semipermeable membrane, identified above as layer 6, which helps control the velocity of liquid flow therethrough so that, if the substance is present in a sample, the substance in the sample detectably reacts with the reactive reagent;

c. a third section, referred to as the lower assembly, comprising the layers identified above as layer 6, which is the semipermeable membrane, and layer 7, which is the superabsorbent composite layer, which is attached underneath the well and comprises a polymeric superabsorbent material impregnated with a reagent, such as a chromogenic dye, which can produce a signal directly proportional to the concentration of a test substance in the liquid sample received in the well, with the superabsorbent material having an absorptive capacity of at least about 200 mL distilled water/100 $cm^2$; the third section also including a backing beneath the superabsorbent layer material for supporting the superabsorbent material, the backing and the superabsorbent layer being sufficiently transparent to the signal when wet so that any signal produced can be detected by reading the signal through the wet backing;

d. a conjugated molecule, such as an antibody-enzyme conjugate capable of specifically binding to the test substance, or a conjugate of a test substance and an enzyme, wherein the conjugated molecule is within the first or second section, and wherein the chromogenic dye of layer 7 is a substrate for the enzyme;

the reactive reagent being a binding partner for the conjugated molecule, and the binding partner being selected from among:

(i) an antibody capable of specifically binding the conjugate of the test substance and the enzyme; and (ii) the test substance;

one improvement comprising:

the first, second and third sections are formed from a series of layers of material each of which is laminated to the other, and wherein the wells in the first section are formed by laminating a series of layers to each other, the series of layers having holes formed therein such that when the holes in each of the series of layers are registered with each other upon laminating of the respective layers to each other, wells for accepting a fluid sample are formed.

The subject invention also concerns a novel composition comprising a semi-permeable membrane, as described for layer 6, and a superabsorbent layer, as described for layer 7 of the subject device, that are laminated together. Any suitable means of laminating the semi-permeable membrane and the superabsorbent layer together can be used. The novel composition of the laminated semi-permeable membrane and superabsorbent layer can be used in assay devices such as those described herein.

All publications and patents cited herein are incorporated by reference in their entirety.

It should be understood that the examples and embodiments described herein are only for illustrative purposes and to teach the best mode, and that various modifications or changes in light thereof will be suggested to persons skilled in the art and are to be included within the spirit and purview of this application and the scope of the appended claims.

What is claimed is:

1. A modular microassay device comprising an upper card assembly and a lower card assembly which can be combined to form a microassay card, wherein said upper card assembly is usable for any microassay card so long as imprinted instructions thereon are modified, and wherein said upper card assembly comprises several layers with concentric holes in each layer such that a test sample can be placed in the wells formed by the alignment of the concentric holes in the several layers of the upper card assembly, said layer comprising:

(a) an imprintable label which may be absent if the subsequent layer is imprintable;

(b) a plastic sheet;

(c) a high tack, pressure-sensitive adhesive, wherein said adhesive is covered by a removable covering;

and said lower card assembly, which can be used for assembly of any microassay card, comprises several layers, said layers comprising:

(d) a plastic sheet with concentric holes that match those in said upper card assembly;

(e) a semi-permeable membrane;

(f) a superabsorbent material;

(g) a plastic sheet with concentric holes that match those in said upper card assembly; and (h) a layer of test-substance-specific material, which has no holes, for interposition between said upper card and lower card assemblies prior to final assembly of the upper and lower card assemblies to form the complete microassay device.

2. The microassay device of claim 1, wherein said layers of said upper card assembly are laminated to each other so as to form a modular upper card assembly, with each layer thereof being in intimate contact with every other layer thereof, and wherein said layers of said lower card assembly are laminated to each other so as to form a modular lower card assembly with each layer thereof being in intimate contact with every other layer thereof.

3. The microassay device of claim 1, wherein said superabsorbent material further comprises a chromogenic enzyme substrate.

4. The microassay device of claim 1, wherein said superabsorbent material is sandwiched between polymeric layers.

5. The microassay device of claim 4, wherein said polymeric layers are selected from the group consisting of cellulose and polyester.

6. The microassay device of claim 1, wherein said semipermeable membrane and said superabsorbent material are laminated together.

7. A modular microassay device comprising an upper card assembly and a lower card assembly which can be combined to form a microassay card, wherein said upper card assembly is usable for any microassay card so long as imprinted instructions thereon are modified, and wherein said upper card assembly comprises several layers with concentric holes in each layer such that a test sample can be placed in the wells formed by the alignment of the concentric holes in the several layers of the upper card assembly, said layers comprising:

(a) an imprintable label which may be absent if the subsequent layer is imprintable; and (b) a plastic sheet;

and said lower card assembly, which can be used for assembly of any microassay card, comprises several layers, said layers comprising:

(c) a high tack, pressure-sensitive adhesive, wherein said adhesive is covered by a removable covering;

(d) a plastic sheet with concentric holes that match those in said upper card assembly;

(e) a semi-permeable membrane;

(f) a superabsorbent material;

(g) a plastic sheet with concentric holes that match those in said upper card assembly; and (h) a layer of test-substance-specific material, which has no holes, for interposition between said upper card and lower card assemblies prior to final assembly of the upper and lower card assemblies to form the complete microassay device.

8. The microassay device of claim 7, wherein said layers of said upper card assembly are laminated to each other so as to form a modular upper card assembly, with each layer thereof being in intimate contact with every other layer thereof, and wherein said layers of said lower card assembly are laminated to each other so as to form a modular lower card assembly with each layer thereof being in intimate contact with every other layer thereof.

9. The microassay device of claim 7, wherein said superabsorbent material further comprises a chromogenic enzyme substrate.

10. The microassay device of claim 7, wherein said superabsorbent material is sandwiched between polymeric layers.

11. The microassay device of claim 10, wherein said polymeric layers are selected from the group consisting of cellulose and polyester.

12. The microassay device of claim 7, wherein said semipermeable membrane and said superabsorbent material are laminated together.

13. The modular microassay device comprising an upper card assembly and a lower card assembly which can be combined to form a microassay card, wherein said upper card assembly is usable for any microassay card so long as imprinted instructions thereon are modified, and wherein said upper card assembly comprises several layers with concentric holes in each layer such that a test sample can be placed in the wells formed by the alignment of the concentric holes in the several layers of the upper card assembly, said layers comprising:

(a) an imprintable label which may be absent if the subsequent layer is imprintable;

(b) a plastic sheet; and (c) a high tack, pressure-sensitive adhesive, wherein said adhesive is covered by a removable covering;

and said lower card assembly, which can be used for assembly of any microassay card, comprises several layers, said layers comprising:

(d) a high tack, pressure-sensitive adhesive, wherein said adhesive can be covered by a removable covering;

(e) a plastic sheet with concentric holes that match those in said upper card assembly;

(f) a semi-permeable membrane;

(g) a superabsorbent material;

(h) a plastic sheet with concentric holes that match those in said upper card assembly; and (i) a layer of test-substance-specific material, which as no holes, for interposition between said upper card and lower card assemblies prior to final assembly of the upper and lower card assemblies to form the complete microassay device.

14. The microassay device of claim 13, wherein said layers of said upper card assembly are laminated to each other so as to form a modular upper card assembly, with each layer thereof being in intimate contact with every other layer thereof, and wherein said layers of said lower card assembly are laminated to each other so as to form a modular lower card assembly with each layer thereof being in intimate contact with every other layer thereof.

15. The microassay device of claim 13, wherein said superabsorbent material further comprises a chromogenic enzyme substrate.

16. The microassay device of claim 13, wherein said superabsorbent material is sandwiched between polymer layers.

17. The microassay device of claim 16, wherein said polymeric layers are selected from the group consisting of cellulose and polyester.

18. The microassay device of claim 13, wherein said semipermeable membrane and said superabsorbent material are laminated together.

* * * * *

UNITED STATES PATENT AND TRADEMARK OFFICE
CERTIFICATE OF CORRECTION

PATENT NO. : 6,224,831 B1
DATED : May 1, 2001
INVENTOR(S) : Alan P. Stafford, H. Kevin Smith, David Yarnes It is certified that error appears in the above-identified patent and that said Letters Patent is hereby corrected as shown below:

<u>Column 6,</u>
Line 5, "layer S" should read -- layer 5 --.
Line 11, "layers 58" should read -- layers 5-8 --.
Line 63, "Alteratively" should read -- Alternatively --.

<u>Column 10,</u>
Line 62, "considered If" should read -- considered. If --.

Signed and Sealed this

Thirtieth Day of October, 2001

*Attest:*

*Attesting Officer*

NICHOLAS P. GODICI
*Acting Director of the United States Patent and Trademark Office*